United States Patent [19]
Kuechler et al.

[11] Patent Number: 6,137,022
[45] Date of Patent: Oct. 24, 2000

[54] PROCESS FOR INCREASING THE SELECTIVITY OF A REACTION TO CONVERT OXYGENATES TO OLEFINS

[75] Inventors: Keith H. Kuechler, Friendswood; Hsiang-ning Sun, Houston, both of Tex.; William Kuechler, Hilton Head, S.C.

[73] Assignee: Exxon Chemical Patents Inc, Houston, Tex.

[21] Appl. No.: 09/333,278

[22] Filed: Jun. 15, 1999

Related U.S. Application Data

[63] Continuation-in-part of application No. 08/984,662, Dec. 3, 1997, abandoned.

[51] Int. Cl.$^7$ .............................. C07C 1/00; C07C 1/20; C07C 1/32
[52] U.S. Cl. .......................... 585/638; 585/639; 585/640
[58] Field of Search .................................... 585/638, 639, 585/640

[56] References Cited

U.S. PATENT DOCUMENTS

| | | | |
|---|---|---|---|
| 4,440,871 | 4/1984 | Lok et al. | 502/214 |
| 4,499,327 | 2/1985 | Kaiser | 585/640 |
| 4,524,234 | 6/1985 | Kaiser | 585/638 |
| 4,677,242 | 6/1987 | Kaiser | 585/638 |
| 4,677,243 | 6/1987 | Kaiser | 585/638 |
| 4,752,651 | 6/1988 | Kaiser | 585/640 |
| 4,814,541 | 3/1989 | Lewis | 585/640 |
| 4,861,938 | 8/1989 | Lewis et al. | 585/640 |
| 5,095,163 | 3/1992 | Barger | 585/640 |
| 5,191,141 | 3/1993 | Barger et al. | 585/640 |
| 5,714,662 | 2/1998 | Vora et al. | 585/640 |
| 5,714,663 | 2/1998 | Serrand et al. | 585/648 |
| 5,914,433 | 6/1999 | Marker | 585/313 |
| 5,952,538 | 9/1999 | Vaughn et al. | 585/640 |

FOREIGN PATENT DOCUMENTS

WO 97/21652  6/1997  WIPO.

OTHER PUBLICATIONS

Methanol Conversion to Light Olefins (Clarence D. Chang) (1984).
Production of Chemicals from Methanol (Warren W. Kaeding & Stephen A. Butter) (1980).
Converting Natural Gas to Ethylene and Propylene by the UOP/Hydro MTO Process (Barger et al.) (12$^{th}$ International Zeolite Conference, 1999 Materials Research Society).
B. B. Singh, et al., "Catalytic Conversion of Methanol to Low Molecular Weight Olefins," *Chem. Eng. Commun.* vol. 4, pp. 749–758 (1980).
I. Balkrishnan et al., "Catalytic Activity and Selectivity in the Conversion of Methanol to Light Olefins," *Journal of Molecular Catalysis*, vol. 17 (1982) pp. 261–270.
C. D. Chang, "Hydrocarbons from Methanol," *Catal. Rev.—Sci. Eng.*, 25(1), pp. 1–118 (1983).
A.N. Rene Bos, et al., "Conversion of Methanol to Lower Olefins. Kinetic Molding, Reactor Simulation, and Selection," *Ind. Eng. Chem. Res.* 1995, 34, pp. 3808–3816.

Primary Examiner—Walter D. Griffin
Attorney, Agent, or Firm—Bradley A. Keller

[57] ABSTRACT

Disclosed is a method of making an olefin product from an oxygenate feedstock comprising, contacting the feedstock in a reaction zone containing 15 volume percent or less of a catalyst, preferably a catalyst comprising a silicoaluminophosphate molecular sieve. In order to obtain the desired product content, i.e., an olefin product having a low level of by-products, conversion of the feedstock in the 15 volume percent or less reaction zone should be maintained between 80 wt % and 99 wt % at the conditions effective to convert 100 wt % of the feedstock when the reaction zone contains at least 33 volume percent of the catalyst material.

14 Claims, No Drawings

PROCESS FOR INCREASING THE SELECTIVITY OF A REACTION TO CONVERT OXYGENATES TO OLEFINS

This is a continuation-in-part of application Ser. No. 08/984,662, filed on Dec. 3, 1997, now abandoned.

FIELD OF THE INVENTION

The present invention relates to a method of making an olefin product from an oxygenate feedstock. In particular, the method concerns contacting the feedstock in a reaction zone containing 15 volume percent or less of a catalyst such that fewer undesirable by-products are formed.

BACKGROUND OF THE INVENTION

Light olefins, defined herein as ethylene, propylene, and butylene, serve as feeds for the production of numerous chemicals. Olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the selectivity of the reaction to ethylene and/or propylene.

ZSM-5 was the first and most extensively studied catalyst for the conversion of methanol to olefins. Unfortunately, ZSM-5 produces not only the desired light olefins, but also undesired by-products. In particular, ZSM-5 produces aromatics, particularly at high methanol conversion. Catalysts are needed which do not produce large amounts of unwanted by-products, such as aromatics, methane, carbon monoxide, and hydrogen gas.

Zeolites with a small pore size have a higher selectivity to lower alkenes, even at 100 mol % methanol conversion. Unfortunately, small pore zeolites are rapidly deactivated during the conversion process. Rapid deactivation can be avoided and high selectivity to light olefins maintained by using a catalyst with a larger pore size but also with lower acidity. Such catalysts still have the downfall of producing undesirable aromatic by-products.

In order to avoid both rapid deactivation of the catalyst and the production of undesirable by-products, catalysts are needed which have both small pore size and intermediate acidity.

SUMMARY OF THE INVENTION

In order to overcome the problems inherent in the prior art, this invention provides a method of making an olefin product from an oxygenate feedstock. The method comprises contacting the feedstock in a reaction zone containing 15 volume percent or less of a catalyst comprising a silicoaluminophosphate molecular sieve material, and maintaining conversion of the feedstock between 80% and 99% under conditions effective to convert 100% of the feedstock when the reaction zone contains at least 33 volume percent of the molecular sieve material. Preferably, the 15 volume percent of the catalyst is distributed throughout the reaction zone. It can be distributed as a multilayer fixed bed or in a homogeneous fashion, including distribution as a fluidized bed or a flowing bed fashion. Preferably, the 33 volume percent of the catalyst is homogeneously dispersed throughout the reaction zone.

In a preferred embodiment the catalyst comprises a silicoaluminophosphate selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and the metal substituted forms thereof. The catalyst can also include a binder material.

In yet another preferred embodiment, the catalyst is contacted with the oxygenate feedstock in the reaction zone at a WHSV of from 1 $hr^{-1}$ to 1000 $hr^{-1}$. It is also preferred that the oxygenate feedstock be selected from the group consisting of methanol; ethanol; n-propanol; isopropanol; $C_4$–$C_{20}$ alcohols; methyl ethyl ether; dimethyl ether; diethyl ether; di-isopropyl ether; methyl mercaptan; methyl sulfide; methyl amine; ethyl mercaptan; diethyl sulfide; diethyl amine; ethyl chloride; formaldehyde; dimethyl carbonate; dimethyl ketone; acetic acid; n-alkyl amines, n-alkyl halides, n-alkyl sulfides, each having n-alkyl groups comprising between about 3 to 10 carbon atoms; and mixtures thereof.

In another embodiment the invention can be operated at a relative linear velocity of less than 1, calculated at a constant temperature and weight hourly space velocity, wherein relative linear velocity is defined as:

$$\text{Relative Linear Velocity} = \frac{\text{feedstock rate (wt. per hour) at 80-99 wt\% conversion}}{\text{feedstock rate (wt. per hour) at 100 wt\% conversion}}$$

DETAILED DESCRIPTION OF THE INVENTION

In the conversion of oxygenates to light olefins, it is desirable to maximize the production of ethylene and/or propylene and to minimize the production of undesired by-products, such as methane, ethane, propane, carbon dioxide, hydrogen gas, and $C_4$+ materials, including aromatics. Catalyst comprising a silicoaluminophosphate molecular sieve is used in this invention to make the desired products.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These pore sizes are typical of molecular sieves having 8 membered rings.

In general, silicoaluminophosphate molecular sieves comprise a molecular framework of comer-sharing [$SiO_2$], [$AlO_2$], and [$PO_2$] tetrahedral units. This type of framework is effective in converting various oxygenates into olefin products.

The [$PO_2$] tetrahedral units within the framework structure of the molecular sieve of this invention can be provided by a variety of compositions. Examples of these phosphorus-containing compositions include phosphoric acid, organic phosphates such as triethyl phosphate, and aluminophsphates. The phosphorous-containing compositions are mixed with reactive silicon and aluminum-containing compositions under the appropriate conditions to from the molecular sieve.

The [$AlO_2$] tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to from the molecular sieve.

The [$SiO_2$] tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to from the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [$MeO_2$] tetrahedral unit. The [$MeO_2$] tetrahedral unit carries a net electric charge depending on the valence state of the metal substituent. When the metal component has a valence state of +2, +3, +4, +5, or +6, the net electric charge is −2, −1, 0, +1, and +2, respectively. Incorporation of the metal component is typically accomplished adding the metal component during synthesis of the molecular sieve. However, post-synthesis ion exchange can also be used. See, for example, U.S. Ser. No. 08/571,506, now U.S. Pat. No. 5,962,762, in which the description of the post-synthesis ion exchange method is fully incorporated herein by reference.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and the metal substituted forms thereof. Preferred are SAPO-18,SAPO-34,SAPO-35, SAPO-44, and SAPO-47, particularly SAPO-18 and SAPO-34. The molecular sieves can be used alone or in combination.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, however, such as by centrifugation or filtration. The product can also be washed, recovered by the same means and dried.

The molecular sieves may be admixed (blended) with other materials. When blended, the resulting composition is typically referred to as a catalyst, with the catalyst comprising the molecular sieve.

Materials which can be blended with the molecular sieve can be various inert or binder materials. These materials include compositions such as kaolin and other clays, various forms of alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. When blended with inert or binder materials, the amount of molecular sieve which is contained in the final catalyst product ranges from 10 to 90 weight percent, preferably 30 to 70 weight percent. The invention can be accomplished while the molecular sieve is included in a blend of inert and/or binder materials.

The oxygenate feedstock comprises at least one organic compound which contains at least one oxygen atom, such as aliphatic alcohols, ethers, carbonyl compounds (aldehydes, ketones, carboxylic acids, carbonates, and the like), or it may contain at least one compound containing a halide, mercaptan, sulfide, or amine. The aliphatic moiety preferably contains from 1 to 10 carbon atoms and more preferably contains from 1 to 4 carbon atoms. Representative oxygenates include but are not necessarily limited to lower straight and branched chain aliphatic alcohols, their unsaturated counterparts and the nitrogen, halogen and sulfur analogues of such. Examples of suitable compounds include, but are not limited to: methanol; ethanol; n-propanol; isopropanol; $C_4$–$C_{20}$ alcohols; methyl ethyl ether; dimethyl ether; diethyl ether; di-isopropyl ether; methyl mercaptan; methyl sulfide; methyl amine; ethyl mercaptan; diethyl sulfide; diethyl amine; ethyl chloride; formaldehyde; dimethyl carbonate; dimethyl ketone; acetic acid; n-alkyl amines, n-alkyl halides, n-alkyl sulfides, each having n-alkyl groups comprising between about 3 to 10 carbon atoms; and mixtures thereof. Preferred as the oxygenate feedstock are methanol, dimethyl ether, and mixtures thereof.

The method of making the preferred olefin product in this invention can include the additional step of making the oxygenate feedstock from hydrocarbons such as oil, coal, tar sand, shale, biomass and natural gas. Methods for making the feedstock from these compositions are known in the art. The methods include fermentation of the compositions to alcohol or ether, or making synthesis gas from the compositions, then converting the synthesis gas to alcohol or ether. Synthesis gas can be produced using known processes such as steam reforming, autothermal reforming and partial oxidization.

One skilled in the art will appreciate that the olefins produced by the oxygenate-to-olefin conversion reaction of the present invention can be polymerized to form polyolefins. Processes for forming polyolefins from olefins are known in the art. Catalytic processes are preferred. Particularly preferred are metallocene, Ziegler/Natta and acid catalytic systems. Prior to being subjected to a polymerization process, the olefin products are recovered from the products of the oxygenate-to-olefin conversion reaction.

Preferably, the oxygenate feedstock should be contacted in the vapor phase in a reaction zone with the defined molecular sieve catalyst at effective process conditions so as to produce the desired olefins, i.e., an effective temperature, pressure, WHSV (Weight Hourly Space Velocity) and, optionally, an effective amount of diluent, correlated to produce olefins. Alternately, the process may be carried out in a liquid or a mixed vapor/liquid phase. When the process is carried out in the liquid phase or a mixed vapor/liquid phase, different conversions and selectivities of feedstock-to-product may result depending upon the catalyst and reaction conditions.

The temperature employed in the conversion process may vary over a wide range depending, at least in part, on the selected catalyst. Although not limited to a particular temperature, best results will be obtained if the process is conducted at temperatures in the range of from about 200° C. to about 700° C., preferably in the range of from about 250° C. to about 600° C., and most preferably in the range of from about 300° C. to about 500° C. Lower temperatures generally result in lower rates of reaction, and the formation of the desired light olefin products may become markedly slow. However, at higher temperatures, the process may not form an optimum amount of light olefin products, and the coking rate may become too high.

Light olefin products will form—although not necessarily in optimum amounts—at a wide range of pressures, including but not limited to autogeneous pressures and pressures in the range of from about 0.1 kPa to about 100 MPa,. A preferred pressure is in the range of from about 6.9 kPa to about 34 MPa, most preferably in the range of from about 48 kPa to about 0.34 MPa. The foregoing pressures are exclusive of diluent, if any is present, and refer to the partial pressure of the feedstock as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction cycle time may vary from tenths of seconds to a number of hours. The reaction cycle time is largely determined by the reaction temperature, the pressure, the catalyst selected, the weight hourly space velocity, the phase (liquid or vapor), and the selected process design characteristics.

A wide range of weight hourly space velocities (WHSV), defined as weight feed per hour per weight of catalyst, for the feedstock will function in the present invention. The WHSV generally should be in the range of from about 0.01 $hr^{-1}$ to about 5000 $hr^{-1}$, preferably in the range of from about 0.1 $hr^{-1}$ to about 2000 $hr^{-1}$, and most preferably in the range of from about 1 $hr^{-1}$ to about 1000 $hr^{-1}$. The catalyst may contain other materials which act as inerts, fillers, or binders; therefore, the WHSV is calculated on the weight basis of oxygenate and catalyst.

One or more diluents may be fed to the reaction zone with the oxygenates, such that the total feed mixture comprises diluent in a range of from about 1 mol % and about 99 mol %. Diluents which may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Preferred diluents are water and nitrogen.

To minimize the production of undesired by-products it is important to reduce the catalyst concentration per unit volume, while maintaining typical operating parameters, particularly temperature and WHSV. This can be done in a variety of ways known to those of ordinary skill in the art. For example, in a fixed or dense bed system, inert material can be added to the catalyst material to increase the distance between catalyst components. The inert material can be layered with the catalyst material in a manner to increase the overall average distance between catalyst particles. However, it is preferable that the inert material be thoroughly mixed with the catalyst in order to provide a homogeneous spacing of materials. In fluid bed systems, the catalyst will be essentially separated as a result of the fluid medium that is used to fluidize the bed. The fluid bed systems, including riser or flowing catalyst bed designs, are most preferred since these will generally tend to be the most homogeneous catalyst systems.

The feedstock should be contacted in a reaction zone containing 15 volume percent or less of a catalyst material, preferably a catalyst comprising silicoaluminophosphate molecular sieve material. In this invention the reaction zone is the entire zone within the actual reactor in which there is actual contact between catalyst and feedstock or converted feedstock. In a fixed or fluid bed, the reaction zone is the actual volume of the bed. In a riser or flowing bed reactor design, this is the entire volume of the reactor.

In order to obtain the desired product content, i.e., a low level of by-products, conversion of the feedstock in the 15 volume percent or less reaction zone should be maintained between 80 wt % and 99 wt % at the conditions effective to convert 100 wt % of the feedstock when the reaction zone contains at least 33 volume percent of the catalyst material. Evaluating the conversion levels at a constant temperature and weight hourly space velocity (WHSV) operating conditions is preferred. At constant temperature and WHSV there will typically be a corresponding decrease in relative linear velocity of the feed at the 80–99 wt % conversion range relative to that at 100 wt % coversion. When the temperature and WHSV at the 80–99 wt % conversion range is the same as at the 100 wt % coversion range, the relative linear velocity of the feed will be less than 1. Preferably the relative linear velocity at constant temperature and WHSV is 0.001–0.9, more preferably 0.01–0.7, most preferably 0.05–0.5.

In this invention, relative linear velocity is defined as:

$$\text{Relative Linear Velocity} = \frac{\text{feedstock rate (wt. per hour) at 80-99 wt\% conversion}}{\text{feedstock rate (wt. per hour) at 100 wt\% conversion}}$$

This invention results in a significant decrease in undesired by-products. Although feedstock is not completely converted, this lack of complete conversion is more than offset by the significant decrease in unwanted by-products.

It is preferable in this invention that the 15 volume percent or less of the catalyst material be relatively evenly distributed throughout the reaction zone in order to provide a more homogeneous system. This can be done by forming a multilayer fixed or dense type bed with thin alternating layers of inert solid material and catalyst material. However, it is preferable that the inert solid material and catalyst material be homogeneously dispersed throughout the reaction zone. More preferably, the catalyst is homogeneously dispersed as a fluidized bed, most preferably the system will operate as a fast flowing catalyst or riser design.

The invention will be better understood with reference to the following examples, which illustrate, but should not be construed as limiting the present invention.

EXAMPLE 1

A sample of 5.0 cm$^3$ (approximately 2.7 grams) of the SAPO-34 catalyst, '14+20 mesh in size, is mixed with 15 cm$^3$ of 3 mm quartz beads and loaded into a ¾" outer diameter 316 stainless steel tubular reactor which is heated by a three zone electric furnace. The first zone, acting as the preheating zone, vaporizes the feed. The temperature of the center zone of the furnace is adjusted to 450° C. and the exit pressure is maintained at the ambient atmospheric pressure. The bottom zone temperature is set high enough to ensure that the effluent from the reactor remains in the vapor state. The reactor is first purged with nitrogen at 50 cm$^3$/min flow rate for 30 minutes. The feed is pure methanol. The feed is pumped into the reactor and calibrated to give a flow rate of about 10 h$^{-1}$ WHSV (feed rate of 2.7 g./hr.). The effluent is analyzed at pre-determined intervals by an on-line gas chromatograph fitted with both a thermal conductivity detector and a flame ionization detector. The following are the results.

| Conversion of methanol: | 100% |
|---|---|
| Selectivity (wt %) | |
| Methane | 2.7 |
| Ethane | 1.1 |
| Ethylene | 39.4 |
| Propane | 2.0 |
| Propylene | 38.2 |
| $C_4+$ | 16.6 |

EXAMPLE 2

The procedures of Example 1 are repeated except that 1.0 cm$^3$ (approximately 0.6 grams) of the same SAPO-34 catalyst was used and the adjusted feed rate to give a WHSV of 10 h$^{-1}$ was 0.54 g./hr., giving a calculated relative linear velocity of 0.2. The following are the results:

| Conversion of methanol: | 94% |
|---|---|
| Selectivity (wt %) | |
| Methane | 1.9 |
| Ethane | 0.8 |
| Ethylene | 42.3 |
| Propane | 0.9 |
| Propylene | 40.9 |
| $C_4+$ | 13.2 |

EXAMPLE 3

The procedures of Example 1 are repeated except that 0.5 cm$^3$ (approximately 0.3 grams) of the same SAPO-34 catalyst was used and the adjusted feed rate to give a WHSV of 10 h$^{-1}$ was 0.27 g./hr., giving a calculated relative linear velocity of 0.1. The following are the results:

| Conversion of methanol: | 88% |
|---|---|
| Selectivity (wt %) | |
| Methane | 1.7 |
| Ethane | 0.9 |
| Ethylene | 42.1 |
| Propane | 0.7 |
| Propylene | 42.9 |
| $C_4+$ | 11.7 |

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A method of making an olefin product from an oxygenate feedstock comprising, contacting the feedstock in a reaction zone containing 15 volume percent or less of a catalyst comprising a silicoaluminophosphate molecular sieve, and maintaining conversion of the feedstock between 80% and 99% under conditions effective to convert 100% of the feedstock when the reaction zone contains at least 33 volume percent of the SAPO molecular sieve.

2. The method of claim 1, wherein the 15 volume percent or less of the catalyst is distributed throughout the reaction zone.

3. The method of claim 2, wherein the 15 volume percent or less of the catalyst is distributed throughout the reaction zone as a multilayer fixed bed.

4. The method of claim 2, wherein the 15 volume percent or less of the catalyst is distributed homogeneously throughout the reaction zone.

5. The method of claim 4, wherein the 15 volume percent or less of the catalyst is distributed as a fluidized bed.

6. The method of claim 4, wherein the 15 volume percent or less of the catalyst is distributed as a flowing bed.

7. The method of claim 1, wherein the at least 33 volume percent of the catalyst is homogeneously dispersed throughout the reaction zone.

8. The method of claim 1, wherein the catalyst comprises a binder.

9. The method of claim 1, wherein the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal substituted forms thereof, and mixtures thereof.

10. The method of claim 9, wherein the molecular sieve is selected from the group consisting of SAPO-18, SAPO-34, SAPO-35, SAPO-44, SAPO-47, and mixtures thereof.

11. The method of claim 1, wherein the catalyst is contacted with the oxygenate feedstock in the reaction zone at a WHSV of from 1 hr$^{-1}$ to 1000 hr$^{-1}$.

12. The method of claim 1, wherein the oxygenate feedstock is selected from the group consisting of methanol; ethanol; n-propanol; isopropanol; $C_4$–$C_{20}$ alcohols; methyl ethyl ether; dimethyl ether; diethyl ether; di-isopropyl ether; methyl mercaptan; methyl sulfide; methyl amine; ethyl mercaptan; diethyl sulfide; diethyl amine; ethyl chloride; formaldehyde; dimethyl carbonate; dimethyl ketone; acetic acid; n-alkyl amines, n-alkyl halides, n-alkyl sulfides, each having n-alkyl groups comprising between about 3 to 10 carbon atoms; and mixtures thereof.

13. The method of claim 12, wherein the oxygenate feedstock is selected from the group consisting of methanol, dimethyl ether, and mixtures thereof.

14. The method of claim 1, including operating at a relative linear velocity of less than 1, calculated at a constant temperature and weight hourly space velocity, wherein relative linear velocity is defined as:

$$\text{Relative Linear Velocity} = \frac{\text{feedstock rate (wt. per hour) at 80-99 wt\% conversion}}{\text{feedstock rate (wt. per hour) at 100 wt\% conversion}}$$

* * * * *

UNITED STATES PATENT AND TRADEMARK OFFICE
CERTIFICATE OF CORRECTION

PATENT NO. : 6,137,022 Page 1 of 1
DATED : October 24, 2000
INVENTOR(S) : Keith H. Kuechler, Hsiang-ning Sun and William Kuechler It is certified that error appears in the above-identified patent and that said Letters Patent is hereby corrected as shown below:

Column 8,
Line 57, replace "at a WHSV of from 1 $hr^{31\ 1}$ to 1000 $hr^{31\ 1}$" with -- at a WHSV of from 1 $hr^{-1}$ to 1000 $hr^{-1}$ --.

Signed and Sealed this

Twenty-seventh Day of April, 2004

JON W. DUDAS
*Acting Director of the United States Patent and Trademark Office*